United States Patent [19]
Witte et al.

[11] 4,189,558
[45] Feb. 19, 1980

[54] PROCESS FOR THE PRODUCTION OF BUTADIENE-PROPYLENE COPOLYMERS

[75] Inventors: Josef Witte, Cologne; Gerd Sylvester, Leverkusen; Gunter Marwede, Cologne, all of Fed. Rep. of Germany

[73] Assignee: Bayer Aktiengesellschaft, Fed. Rep. of Germany

[21] Appl. No.: 907,185

[22] Filed: May 18, 1978

Related U.S. Application Data

[63] Continuation-in-part of Ser. No. 876,649, Feb. 10, 1978, abandoned.

[30] Foreign Application Priority Data

Feb. 14, 1977 [DE] Fed. Rep. of Germany ....... 2706118

[51] Int. Cl.² ............................................. C08F 4/68
[52] U.S. Cl. ........................... 526/169.2; 260/32.8 A; 260/33.2 R; 260/33.6 A; 526/339

[58] Field of Search ...................... 526/169.2, 172, 339

[56] References Cited

U.S. PATENT DOCUMENTS

| 3,652,518 | 3/1972 | Kawasaki et al. | 526/339 |
| 3,652,519 | 3/1972 | Kawasaki et al. | 526/169.2 |
| 3,824,224 | 7/1974 | Kawasaki et al. | 526/339 |

Primary Examiner—Stanford M. Levin
Attorney, Agent, or Firm—Connolly and Hutz

[57] ABSTRACT

A process for the production of strictly alternating copolymers of trans-1,4-butadiene and propylene units by the solution copolymerization of butadiene and propylene with vanadium-containing organometallic mixed catalysts, wherein vanadyl dialkoxy halides of which the alkoxy groups are branched in the 2-position to the oxygen atom are used as the vanadium compounds.

3 Claims, No Drawings

PROCESS FOR THE PRODUCTION OF BUTADIENE-PROPYLENE COPOLYMERS

CROSS-REFERENCE TO RELATED APPLICATION

This application is a continuation-in-part of application Ser. No. 876,649 filed Feb. 10, 1978 and now abandoned.

This invention relates to a process for the production of copolymers of butadiene and propylene having a strictly alternating structure.

According to works of FURUKAWA (Angew. Makromol. Chemie 23, 189 (1972), strictly alternating copolymers of butadiene and propylene can be produced by using certain vanadium-containing organometallic mixed catalysts. However, despite extensive research work, it has not yet proved possible to produce polymers which are made up of strictly alternating propylene and trans-1,4-butadiene units and which have sufficiently high molecular weights to be suitable for use as synthetic rubber.

Although it is possible to produce propylene-butadiene copolymers having relatively high molecular weights with certain titanium-containing organometallic mixed catalysts, these copolymers show only a relatively low degree of alternation. In addition, the butadiene units are no longer present solely in the trans-1,4-configuration, but also in the cis-1,4- and 1,2-configurations. Accordingly, these products have a considerably poorer range of properties. Furthermore, gel formation readily occurs with titanium catalysts.

All hitherto described catalyst systems for the alternating copolymerisation of butadiene and propylene are also attended by two major disadvantages. Firstly, the activities are too low for commercial use; in other words, the consumption of catalyst is too high. Secondly, all the systems have to be produced at very low temperatures (−78° C.). If the catalysts are preformed at elevated temperatures, for example in the range of from −40° C. to −30° C., they again suffer losses of activity and produce polymers with a reduced trans-1,4-butadiene content and a relatively low degree of alternation.

J. FURUKAWA (loc. cit.) has described the production of butadiene-propylene copolymers with a number of vanadium- and titanium-containing mixed catalysts. The best catalyst systems are

and

The titanium system gives a conversion of 49% by weight in 17 hours at −45° C. The catalyst has to be produced and preformed at −78° C. At least 6 mMoles of transition metal compound are required for producing 100 g of polymer.

An object of the present invention is to provide an improved process and an improved catalyst for the production of copolymers with an alternating structure of trans-1,4-butadiene and propylene units.

It has been found that vanadium catalysts with considerably higher activity for the alternating copolymerisation of propylene and butadiene are obtained by using vanadyl dialkoxy halides VO(OR)$_2$Hal whose alkyl radicals R are the same or different and are branched in the 2-position, for example isobutyl radicals and, with particular preference, 2,2-dimethyl propyl radicals, as the transition metal compound. In combination with aluminium trialkyl, preferably aluminium triisobutyl, these vanadium compounds give catalysts which are active without having to be preformed.

The present invention provides a process for the production of strictly alternating copolymers of trans-1,4-butadiene and propylene units by the solution copolymerisation of butadiene and propylene with organometallic mixed catalysts containing vanadium compounds, wherein vanadyl dialkoxy halides whose alkoxy groups are branched in the 2-position to the oxygen atom are used as the vanadium compounds.

Suitable vanadium compounds correspond to the general formula:

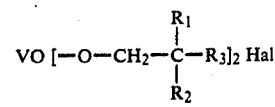

in which
R$_1$ each independently represents hydrogen or C$_1$–C$_4$-alkyl,
R$_2$ each independently represents C$_1$–C$_4$-alkyl,
R$_3$ each independently represents C$_1$–C$_8$-alkyl, and
Hal represents chlorine or bromine.

The vanadium compounds are produced by reacting vanadium oxyhalides with the corresponding branched alcohols, (cf.Example 1). Generally from 0.1 to 1 mMole and preferably from 0.3 to 0.6 mMole of vanadium compound are used per 100 g of monomer mixture for polymerisation.

In cases where, for example, 0.3 mMole of vanadium compound are used with 100 g of an equimolar mixture of butadiene and propylene, a conversion of more than 90% by weight is obtained in 3 hours at −50° C. The copolymers have Mooney viscosities ML-4′100° C. of 40–80. In the process of the present invention an aluminium trialkyl is used in combination with the vanadium compounds as the organometallic mixed catalyst. The aluminium trialkyl corresponds to the formula AlR$_3$, wherein R represents an alkyl radical having from 1 to 8 carbon atoms. Suitable aluminium compounds are e.g. Al(CH$_3$)$_3$, Al(C$_2$H$_5$)$_3$, Al(i-C$_3$H$_7$)$_3$, Al(n-C$_8$H$_{17}$)$_3$, and, preferably, Al(i-C$_4$H$_9$)$_3$.

The molar ratio of aluminium trialkyl to vanadyl dialkoxy halide in the organometallic mixed catalyst is from 2:1 to 15:1 and preferably from 4:1 to 8:1.

The process is carried out by solution polymerization. Suitable solvents are aromatic, cycloaliphatic or aliphatic hydrocarbons, for example toluene, cyclopentane and hexane, and also chlorinated hydrocarbons, such as dichloromethane. Butadiene and propylene are generally used in equimolar quantities.

An excess of propylene of around 10% mole does not interfere with the polymerisation reaction. The monomer concentration is generally in the range of from 10 to 30% by weight and preferably from 20 to 25% by weight. Preferred solvents are aliphatic hydrocarbons, such as butane, pentane and hexane.

The solvent-monomer mixture is cooled to the reaction temperature. The reaction temperature is generally in the range of from −70° C. to −20° C. and preferably from −40° C. to −50° C. The catalyst components are then added. The order in which they are added is not critical. The catalyst components are normally used in 0.5 to 2 molar hydrocarbon solution. The polymerisation reaction begins immediately, as reflected in an increase in the viscosity of the solution. The final conversion is reached after 2 to 5 hours. In general, it amounts to more than 90% by weight. The organometallic mixed catalyst is then deactivated in the usual way by adding amines, alcohols or carboxylic acids, such as ethylene diamine, dipropylene triamine, ethanol or isopropanol. Following the addition of an antioxidant, for example 2,6-di-tert.-butyl methyl phenol, the copolymer is isolated from the solution by precipitation with a non-solvent, such as ethanol or isopropanol, or even by steam distillation of the solvent. The rubber-like copolymer is dried in a drying cabinet or in a screw machine. The entire process, i.e. polymerisation and working up, may be carried out either continuously or in batches.

The copolymer is strictly alternating and has the following structure

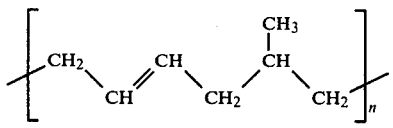

This structure has been reliably confirmed by $_1$H-NMR, $_{13}$C-NMR and IR-spectroscopic examinations.

The copolymers produced according to the invention are suitable for use as synthetic rubber. They may readily be processed in the standard machines of the rubber industry, such as mixing rolls, internal mixers and calenders. The vulcanisates show outstanding strength properties and may be used for the production of motor vehicle tyres and commercial rubber articles. The invention is illustrated by the following examples.

EXAMPLE 1

Production of the vanadium compounds 50 mMole of vanadium oxychloride and 50 ml of anhydrous toluene are initially introduced into a 250 ml capacity three-necked flask equipped with a reflux condenser, stirrer, dropping funnel and nitrogen inlet pipe. 100 mMole of alkanol dissolved in 40 ml of toluene are then added dropwise over a period of 20 minutes at room temperature. The reaction mixture is then stirred for 5 hours at room temperature to complete the reaction. Throughout the entire period, a moderate stream of nitrogen is passed through the solution to remove the hydrogen chloride formed. The gas stream is passed through 150 ml of 1 N NaOH.

The quantity of hydrogen chloride removed is determined by titration. The solution of the vanadium compound is brought to a volume of 100 ml with dry toluene. The solutions obtained can be stored indefinitely.

Table 1

| VO(OR)$_2$Cl Test number | R—OH R= | Colour of the solution | mMole of HCl formed |
|---|---|---|---|
| 1 | CH$_3$CH$_2$— | light brown | 98 |
| 2 | (CH$_3$)$_2$CH— | light brown | 92 |
| 3 | C$_2$H$_5$(CH$_3$)CH— | light brown | 97 |
| 4 | (CH$_3$)$_2$CH—CH$_2$— | light brown | 98 |
| 5 | (CH$_3$)$_3$C— | yellow, precipitation | 53 |
| 6 | (CH$_3$)$_3$C—CH$_2$— | light brown | 98 |

Polymerisations

EXAMPLE 2

In Example 2, tests 1 to 6, the above mentioned vanadyl dialkoxy chlorides are tested for their suitability as catalyst components. Tests 4 and 6 represent the process according to the invention. Tests 1, 2, 3 and 5 are for comparison.

| Polymerisation recipe | |
|---|---|
| Toluene | 750 ml |
| Butadiene | 92 g = 1.7 moles |
| Propylene | 71 g = 1.7 moles |
| Temperature | −45° C. |
| VO(OR)$_2$Cl | 1 mMole |
| Al(iC$_4$H$_9$)$_3$ | 6 mMole |
| Polymerisation time | 5 h |
| Polymerisation temperature | −45° C. |

The mixture of solvent with monomers is cooled to −45° C. in a stirrer-equipped vessel in the absence of moisture and oxygen. The catalyst components are then added. Polymerisation begins immediately. The temperature is kept at −45° C. by cooling. After 5 hours, a solution of 2 ml of isopropanol and 1 g of 2,6-di-tert.-butyl-4-methylphenol in 20 ml of toluene is added and the polymer is precipitated with 3 liters of methanol. The polymer is dried in vacuo at 50° C.

The test results are set out in Table 2.

Table 2

| Test number | VO(OR)$_2$Cl R= | Conversion % by weight | [η]dl/g in toluene at 25° C. | Soluble in ether | methylethyl ketone |
|---|---|---|---|---|---|
| 1 | CH$_3$CH$_2$— | 2 | — | — | — |
| 2 | (CH$_3$)$_2$CH— | 4 | 0.81 | 80% | 20% |
| 3 | C$_2$H$_5$(CH$_3$)CH— | 10 | 1.16 | — | — |
| 4 | (CH$_3$)$_2$—CH—CH$_2$— | 31 | 1.28 | 100% | 0% |
| 5 | (CH$_3$)$_3$C— | 9 | 0.72 | — | — |
| 6 | (CH$_3$)$_3$—C—CH$_2$— | 84 | 1.37 | 100% | 0% |

It can be seen from the data of Table 2 that conversions of more than 10% are only obtained with the vanadium compounds used according to the invention. Test 6 clearly demonstrates the surprising advantages of the preferred vanadium compound VO[OCH$_2$-C(CH$_3$)$_3$]$_2$Cl.

EXAMPLE 3

Catalyst production (a) Vanadium catalyst (according to Angew. Makromol, Chemie 23, pages 190–191 (1972)

| VOCl$_3$ (1 molar in toluene) | 4 ml = 4 mMole |

-continued

| | |
|---|---|
| VO(OC$_2$H$_5$)$_3$ (1 molar in toluene) | 6 ml = 6 mMole |
| Toluene | 15 ml |
| Temperature °C. | −78 |
| Al(iC$_4$H$_9$)$_3$ 1 molar in toluene | 25 ml = 25 mMole |

Added dropwise over a period of 15 minutes at −78° C.

(b) Titanium catalyst (according to Angew. Makromol. Chemie 23, pages 192–193 (1972)

| | |
|---|---|
| TiCl$_4$ (1 molar in toluene) | 10 ml = 10 mMole |
| Acetophenone (1 molar in toluene) | 10 ml = 10 mMole |
| Toluene | 50 ml |
| Temperature °C. | −78 |
| Al(i-C$_4$H$_9$)$_3$ 1 M in toluene | 30 ml = 30 mMole |

Added dropwise over a period of 20 minutes at −78° C.

(c) Polymerisation, carried out in accordance with Example 2.

TABLE 3

| Test number | 1 | 2 | 3 | 4 |
|---|---|---|---|---|
| Toluene | 30 ml | 750 ml | 750 ml | 750 ml |
| Butadiene | 92 g | 92 g | 92 g | 92 g |
| Propylene | 71 g | 71 g | 71 g | 71 g |
| Temperature °C. | −45 | −45 | −45 | −45 |
| VO[OCH$_2$—C(CH$_3$)$_3$]$_2$Cl | 1mMole | — | — | — |
| Al(i-C$_4$H$_9$)$_3$ | 6mMole | — | — | — |
| Preformed catalyst (a) | — | 30ml+ | 5ml++ | — |
| Preformed catalyst (b) | — | — | — | 60 ml+++ |
| Polymerisation temperature | −45° | −45° | −45° | −45° |
| Polymerisation time h | 3 h | 3 h | 16 h | 16 h |
| Conversion % by weight | 92 | 31 | 2 | 42 |
| [η]dl/g toluene, 25° | 1.56 | 0.68 | — | 1.42 |
| Mooney value [ML-4′ 100° C.] | 42 | 10 | — | 24 |

+6 mMole of vanadium compound
++1 mMole of vanadium compound
+++6 mMole of titanium compound.

Tests 2, 3 and 4 (Comparison Tests) produce much lower conversions than test 1 according to the invention. The microstructures of test products 1, 2 and 4 are shown in Table 4.

Table 4

| Example 3 Test number | Mole % of butadiene | Mole % of propylene | Butadiene structure % | | |
|---|---|---|---|---|---|
| | | | trans-1,4 | cis 1,4 | 1,2 |
| 1 | 50 | 50 | 100 | — | — |
| 2 | 50 | 50 | 99 | — | 1 |
| 4 | 54 | 46 | 82 | 14 | 4 |

EXAMPLE 4

Polymerisation in n-hexane as solvent

The following test is carried out in a 6 liter stirrer-equipped autoclave in the same way as described in Example 2:

| | |
|---|---|
| Hexane | 3000 ml |
| Butadiene | 380 g |
| Propylene | 330 g |
| Temperature | −45° C. |
| VO[OCH$_2$—C(CH$_3$)$_3$]$_2$Cl 0.5 M in toluene | 6 ml = 3 mMole |
| Al(iC$_4$H$_9$)$_3$ 1.0 M in toluene | 20 ml = 20 mMole |
| Polymerisation temperature | −40° C. |
| Polymerisation time | 5 h |
| Conversion | 84% by weight |
| Mooney value [ML-4′ 100° C.] | 45 |

We claim:

1. A process for producing an alternating copolymer of trans-1,4-butadiene and propylene which comprises solution copolymerization of butadiene and propylene in the presence of a catalyst consisting of a vanadyl dialkoxy halide whose alkoxy groups are branched at the 2-position to the oxygen atom and AlR$_3$ wherein R is alkyl having from 1 to 8 carbon atoms, the molar ratio of AlR$_3$ to said vanadyl dialkoxy halide being from 2:1 to 15:1.

2. The process of claim 1 wherein the vanadyl dialkoxy halide is of the formula

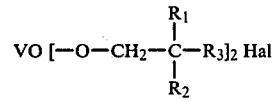

wherein each R$_1$ independently is hydrogen or C$_{1-C4}$ alkyl, each R$_2$ independently is C$_{1-C4}$ alkyl, each R$_3$ independently is C$_1$-C$_8$ alkyl and Hal is chlorine or bromine.

3. The process of claim 2 wherein each R$_1$, R$_2$ and R$_3$ is methyl and Hal is chlorine.

* * * * *